(12) United States Patent
Schreiber

(10) Patent No.: US 7,394,063 B2
(45) Date of Patent: Jul. 1, 2008

(54) MICROSCOPE FOR INVESTIGATING THE LIFETIME OF EXCITED STATES IN A SAMPLE

(75) Inventor: Frank Schreiber, Dossenheim (DE)

(73) Assignee: Leica Microsystems CMS GmbH, Wetzlar (DE)

( * ) Notice: Subject to any disclaimer, the term of this patent is extended or adjusted under 35 U.S.C. 154(b) by 0 days.

(21) Appl. No.: 11/106,193

(22) Filed: Apr. 14, 2005

(65) Prior Publication Data

US 2005/0230610 A1 Oct. 20, 2005

(30) Foreign Application Priority Data

Apr. 14, 2004 (DE) .................. 10 2004 017 956

(51) Int. Cl.
*G02B 21/06* (2006.01)
*G01N 21/64* (2006.01)
*H01J 3/14* (2006.01)

(52) U.S. Cl. ................... 250/234; 250/458.1

(58) Field of Classification Search ................ 250/205, 250/234, 458.1, 459.1; 359/369–398; 430/139, 430/396; 356/318
See application file for complete search history.

(56) References Cited

U.S. PATENT DOCUMENTS

| 5,212,099 | A | * | 5/1993 | Marcus | 436/172 |
| 5,909,278 | A | * | 6/1999 | Deka et al. | 356/318 |
| 6,356,088 | B1 | * | 3/2002 | Simon et al. | 324/752 |
| 6,697,196 | B2 | * | 2/2004 | Suzuki | 359/385 |
| 6,741,346 | B1 | * | 5/2004 | Gerstner et al. | 356/318 |
| 6,903,347 | B2 | * | 6/2005 | Baer | 250/492.2 |

FOREIGN PATENT DOCUMENTS

| DE | 101 44 435 | 4/2003 |
| EP | 0 681 695 | 5/1997 |

OTHER PUBLICATIONS

D.W. Piston et al., "Two-photon-excitation fluorescence imaging of three-dimensional calcium-ion activity", Applied Optics, vol. 33, No. 4, Feb. 1, 1994, pp. 662-669.
D.W. Piston et al., "Time-Resolved Fluorescence imaging and Background Rejection by Two-Photon Excitation in Laser Scanning Microscopy", SPIE vol. 1640, Time Resolved Laser Spectroscopy in Biochemistry III (1092), pp. 381-389.

* cited by examiner

*Primary Examiner*—John R Lee
(74) *Attorney, Agent, or Firm*—Darby & Darby

(57) ABSTRACT

A microscope for investigating the lifetime of excited states in a sample has a light source that generates excitation light, and has a detector that receives detected light proceeding from the sample. The light source contains a semiconductor laser which emits pulsed excitation light. An adjusting apparatus is provided for adjusting the pulse repetition rate to the specific lifetime properties of the sample.

18 Claims, 2 Drawing Sheets

MICROSCOPE FOR INVESTIGATING THE LIFETIME OF EXCITED STATES IN A SAMPLE

CROSS REFERENCE TO RELATED APPLICATIONS

This application claims priority to German patent application 10 2004 017 956.5, the entire disclosure of which is hereby incorporated by reference herein.

FIELD OF THE INVENTION

The invention concerns a microscope for investigating the lifetime of excited states in a sample.

BACKGROUND OF THE INVENTION

By investigating the lifetime of the excited states of a sample or a fluorophore, important conclusions can be drawn as to the properties of the sample. Especially when multiple fluorescent dyes are used, identification and distinction of the fluorophores becomes possible using fluorescence lifetime image microscopy (FLIM).

EP 0 681 695 B1 discloses an apparatus for quantitative imaging of multiple fluorophores. The apparatus contains a means for guiding two scanning beams of continuous electromagnetic radiation of different wavelengths. The intensity of each beam is sinusoidally modulated with various modulation frequencies. The modulated detected radiation is allocated to the respective excitation wavelengths using the lock-in technique.

DE 101 44 435 A1 discloses a method and an arrangement for generating time-resolved and positionally resolved, as well as time- and wavelength-resolved, fluorescence images. The arrangement is based on pulsed fluorescence excitation with a femtosecond or picosecond laser, detection being accomplished in time-correlated and positionally correlated fashion in a single-photon counting system.

In scanning microscopy, a sample is illuminated with a light beam in order to observe the reflected or fluorescent light emitted from the sample. The focus of the illuminating light beam is moved in a specimen plane by means of a controllable beam deflection device, generally by tilting two mirrors, the deflection axes usually being perpendicular to one another so that one mirror deflects in the X direction and the other in the Y direction. Tilting of the mirrors is brought about, for example, by means of galvanometer positioning elements. The power level of the light coming from the specimen is measured as a function of the position of the scanning beam.

In confocal scanning microscopy specifically, a specimen is scanned in three dimensions with the focus of a light beam.

A confocal scanning microscope generally comprises a light source, a focusing optical system with which the light of the source is focused onto an aperture (called the "excitation pinhole"), a beam splitter, a beam deflection device for beam control, a microscope optical system, a detection pinhole, and the detectors for detecting the detected or fluorescent light. The illuminating light is coupled in via a beam splitter. The fluorescent or reflected light coming from the specimen travels back via the beam deflection device to the beam splitter, traverses it, and is then focused onto the detection pinhole behind which the detectors are located. Detected light that does not derive directly from the focus region takes a different light path and does not pass through the detection pinhole, so that a point datum is obtained that results, by sequential scanning of the specimen, in a three-dimensional image. A three-dimensional image is usually achieved by acquiring image data in layers.

In confocal scanning microscopy, a detection pinhole can be dispensed with in the case of two-photon (or multi-photon) excitation, since the excitation probability depends on the square of the photon density and thus on the square of the illuminating light intensity, which of course is much greater at the focus than in the adjacent regions. The fluorescent light being detected therefore very probably originates almost exclusively from the focus region, which renders superfluous any further differentiation, using a pinhole arrangement, between fluorescent photons from the focus region and fluorescent photons from the adjacent regions.

In this case non-descan detection can be performed, in which the detected light does not (as in the case of the descan configuration) travel to the detector via the beam deflection device and through the beam splitter for incoupling illuminating light, but instead is deflected out directly after the objective by means of a dichroic beam splitter, and detected. Arrangements of this kind are known, for example, from the publication of David W. Piston et al., "Two-photon excitation fluorescence imaging of three-dimensional calcium ion activity," Applied Optics, Vol. 33, No. 4, February 1996, and from Piston et al., "Time-Resolved Fluorescence Imaging and Background Rejection by Two-Photon Excitation in Laser Scanning Microscopy," SPIE Vol. 1640.

Lifetime imaging based on time-correlated single-photon measurement is usually implemented using infrared pulsed lasers with a repetition rate of approx. 80 MHz, with multi-photon (usually two-photon) excitation. These pulsed infrared lasers (usually mode-coupled titanium sapphire lasers) are very expensive and very complex. The pulse repetition rate of these lasers depends directly on the resonator length and therefore cannot be varied. With longer-lifetime fluorescent dyes in particular, there is a greater probability that excited fluorophores will not have returned to the ground state by the time the next excitation pulse arrives. Because the next excitation pulse serves as the time base in such cases, this results in incorrect measurement results. A further disadvantage of the known arrangements based on pulsed titanium sapphire lasers derives from the fact that because of their design, titanium sapphire lasers emit excitation light in the region of approximately 800 nm (approx. 720-980 nm), so that only dyes matched specifically to those wavelengths can be investigated and used.

SUMMARY OF THE INVENTION

It is an object of the present invention to provide a microscope for investigating the lifetime of excited states in a sample or a fluorophore that on the one hand makes possible a time-efficient measurement adaptable to the particular fluorophores or samples, and that allows any desired sample dyes to be used with any desired excitation spectra.

The present invention provides a microscope which is characterized in that the light source contains a semiconductor laser which emits pulsed excitation light; and that an adjusting apparatus is provided for adjusting the pulse repetition rate to the specific lifetime properties of the sample.

The invention has the advantage that the pulse repetition rate of the semiconductor laser can be adjusted to the lifetime of the sample dyes being investigated, for example by way of an uncomplicated control system for the electrical pump current. The number of detected photons is thereby advantageously optimized, which ultimately results in a substantially more accurate investigation result in terms of the fluorescence lifetime. Another advantage of the microscope according to the present invention derives from the fact that detection can be accomplished in both the descan and non-descan detection configuration.

Because of the possibility of adapting the repetition rate of the laser to the lifetime of the fluorescent dyes, the effect according to which excited fluorophores have not returned to the ground state by the time the next excitation pulse arrives can be effectively eliminated.

Especially with fluorescent dyes having a short lifetime, there is no waste of unused measurement time. The effect according to which fluorophores, after excitation with a light pulse, have long since returned to the ground state before the next light pulse arrives, can be effectively eliminated according to the present invention.

A further advantage is the fact that semiconductor lasers of any desired output wavelength are usable, so that a restriction no longer exists with regard to the use of sample dyes having excitation spectra in the near infrared region (or in the UV region, for two-photon excitation).

All these advantages are achieved without having to sacrifice the principle of time-correlated single-photon measurement in favor of less-accurate sinusoidal excitation modulation.

In an embodiment, excitation of the sample encompasses a one-photon transition, detection occurring, with this variant, in the descan configuration behind the detection pinhole.

In another embodiment, excitation of the sample is accomplished via a multi-photon transition, for example a two-photon transition. In this variant it is particularly advantageous to perform detection in the non-descan configuration, since less light is lost on this detection path than on the descan detection light path. In order to adapt to specific experimental conditions, however, it is also possible to detect in descan detection configuration with multi-photon excitation.

In an embodiment, the light source contains at least one further semiconductor laser. With this variant, fluorescent dyes having different excitation spectra can be excited simultaneously or sequentially. When there are multiple sample dyes having different lifetimes in the sample, in this variant the repetition rates can be specifically adapted to the individual dyes. A multi-channel detector is preferably used in this variant. It is also possible, however, to excite the sample dyes sequentially using the semiconductor laser and the further semiconductor laser and, in a manner adapted thereto, to perform a sequential detection in a single channel. This variant ensures, in simple and effective fashion, that the dyes being used can be distinguished.

The semiconductor laser and the at least one further semiconductor laser are preferably synchronized with one another. Synchronization in this context can be accomplished in very different ways. On the one hand, the laser pulses can in each case be irradiated simultaneously onto the sample. A sequential setting is also conceivable, for example such that the pulses of the first semiconductor laser always precede the laser pulse of the second semiconductor laser by a previously defined unit of time (e.g. 3 ns). Different cycle timing is also conceivable, such that one laser pulse of the second semiconductor laser is irradiated at every third laser pulse of the first semiconductor laser, etc.

In an embodiment, a control apparatus is provided that controls the pump current operating the semiconductor laser or the further semiconductor laser. The semiconductor lasers can be connected, via an electronic interface, either directly to the PC or to the supply unit of the scanning microscope. This has the advantage that the lasers can be driven directly via the user software of the scanning microscope.

In addition to the semiconductor laser and/or the at least one other semiconductor laser, conventional pulsed laser sources can, of course, also be used. The spectrum of such light sources is particularly broad, encompassing mode-coupled dye or solid-state lasers (Ti:sapphire or Nd lasers), frequency-multiplied mode-coupled beam sources, OPOs, etc.

In an embodiment, the control apparatus generates, synchronously with the pulses of the excitation light or of the further excitation light, electrical detection start signals that allow time-correlated sensing of the detected photons.

The repetition rate of the semiconductor laser and/or the repetition rate of the further semiconductor laser is preferably continuously adjustable. In another variant, the repetition rate of the semiconductor laser and/or the repetition rate of the further semiconductor laser is adjustable in steps. The repetition rates that can be set are preferably in steps to 40 megahertz and/or 20 megahertz and/or 10 megahertz and/or 5 megahertz.

The microscope is preferably embodied as a scanning microscope, in particular as a confocal scanning microscope. Detection with a confocal microscope using descan detection has the advantage of insensitivity to the ambient light that, with non-descan detection, can considerably distort the measurement result. The microscope according to the present invention can advantageously be used for fluorescence resonance energy transfer (FRET) investigations. In FRET excitation, excitation energy is transferred non-radiatively from a donor to an acceptor. When an acceptor is present in the vicinity of a donor, the lifetime of the donor changes; this can be efficiently and accurately measured using the microscope according to the present invention.

BRIEF DESCRIPTION OF THE DRAWINGS

The subject matter of the invention is depicted schematically in the drawings and will be described below with reference thereto.

DETAILED DESCRIPTION OF THE INVENTION

Figure 1:
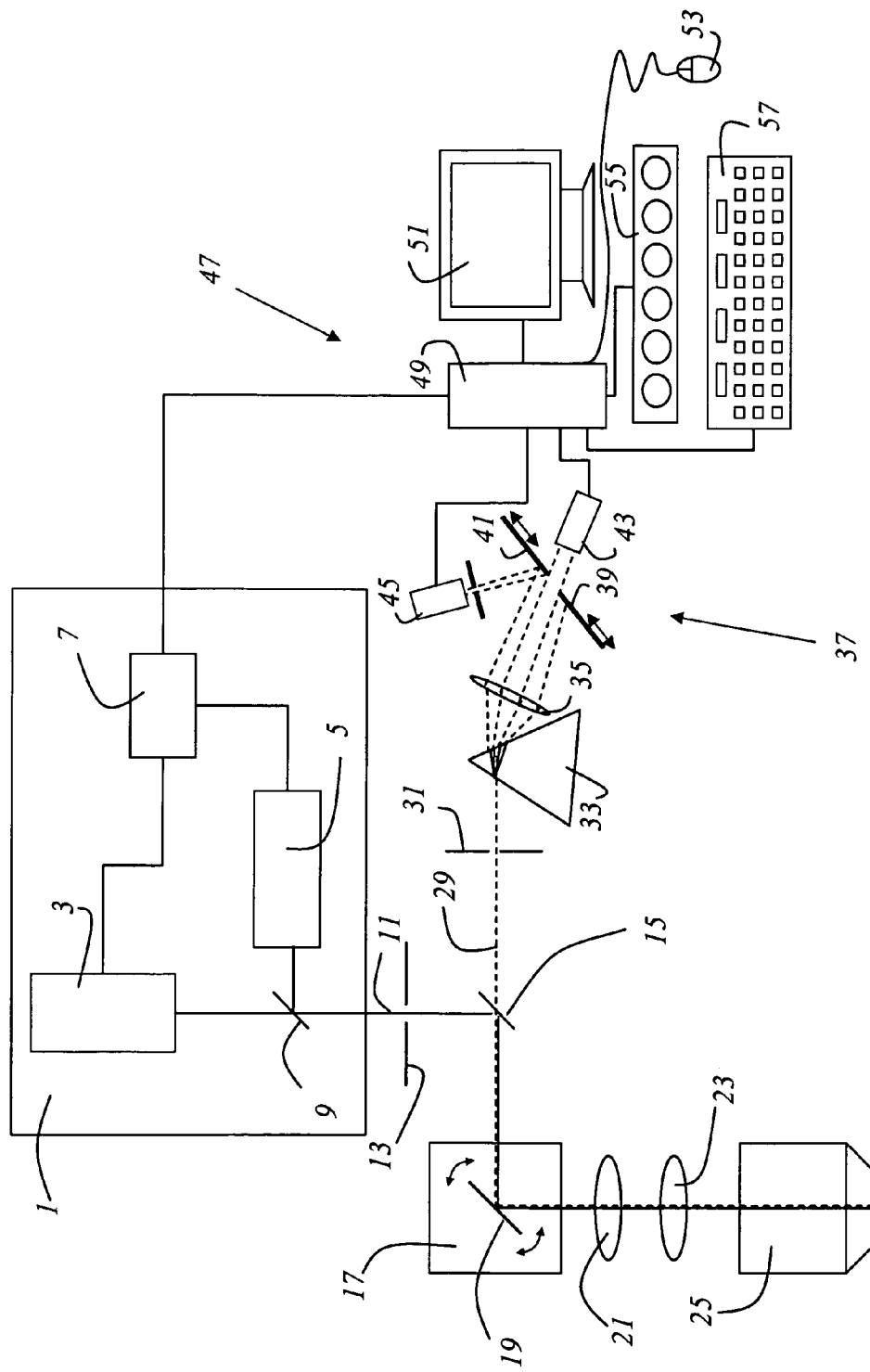
FIG. 1 shows a scanning microscope according to the present invention.

FIG. 1 shows a confocal scanning microscope according to the present invention having a light source 1 that contains a semiconductor laser 3 and a further semiconductor laser 5. The pump current of semiconductor lasers 3, 5 is controlled by a control apparatus 7. The pulsed output light of semiconductor laser 3 and of further semiconductor laser 5 is combined with the aid of a dichroic beam combiner 9 into an excitation light beam bundle 11, and directed onto illumination pinhole 13. The illuminating light beam bundle emerging from illumination pinhole 13 is directed, with the aid of main beam splitter 15, to a beam deflection device 17 that contains a gimbal-mounted scanning mirror 19. Beam deflection device 17 guides illuminating light beam bundle 11 through scanning optical system 21, tube optical system 23, and microscope objective 25, and over or through sample 27. Detected light 29 (shown with dashed lines) proceeding from the sample travels along the same light path, i.e. through microscope objective 25, tube optical system 23, and scanning optical system 21 and via beam deflection device 17 back to main beam splitter 15, traverses the latter and the downstream detection pinhole 31, and arrives at a multi-band detector 37. With the aid of a prism 33, the detected light firstly is spatially spectrally divided. The spatially spectrally divided detected light is focused with the aid of field lens 35 into a focal line. Arranged in the region of the focal line is a slit aperture arrangement that contains a first slit aperture 39 and a second slit aperture 41.

The front sides of slit apertures 39, 41 are embodied reflectively. The light allowed to pass through slit apertures 39, 41 travels via a first detection channel to a first detector 43. The detected light blocked by slit aperture 41 is reflected by the reflectively coated side of second slit aperture 41, and travels via a second detection channel to a second detector 45. First detector 43 and second detector 45 detect in different detection regions. Control apparatus 7 generates, synchronously with the electrical triggering pulses for the first and second semiconductor lasers 3, 5, electrical detection start signals that are transferred to a processing unit 47. Detectors 43, 45 generate electrical signals, proportional to the number of incoming detected photons, that are transferred to processing unit 47. Evaluation of the measured signals occurs in processing unit 47, which is embodied as PC 49. The results are displayed graphically on a monitor 51. With the aid of PC 49 and the adjustment elements connected to it, such as computer mouse 53, panel box 55, and keyboard 57, the user can adjust the pulse repetition rate of first semiconductor laser 3 and second semiconductor laser 5 in sample-specific fashion. The adjustment is preferably accomplished in such a way that no more than one detected photon is generated for each excitation light pulse. The adjustment is preferably performed so as to result in a detection rate of approximately one detected photon for every ten excitation pulses.

Figure 2:
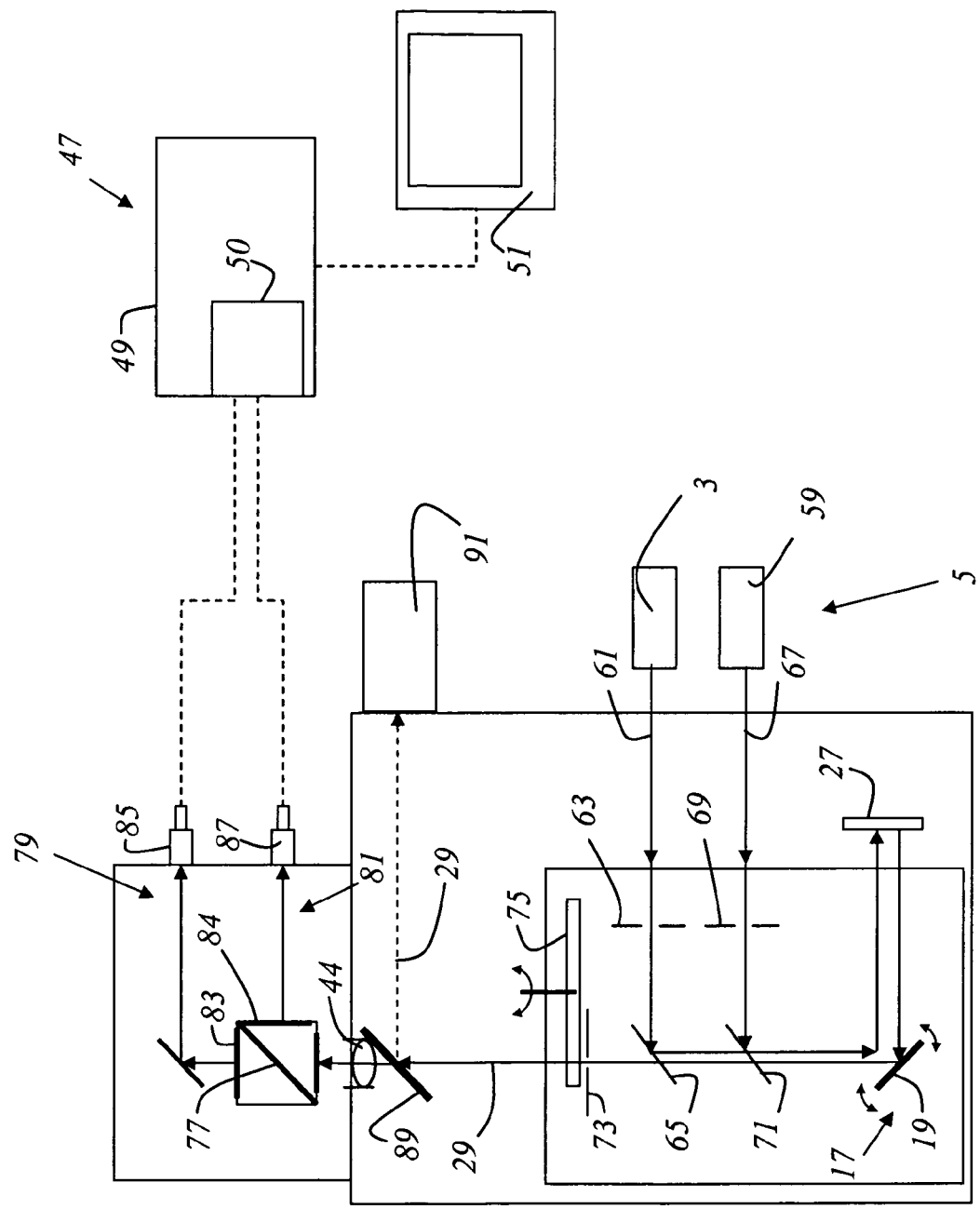
FIG. 2 shows a further scanning microscope according to the present invention.

FIG. 2 shows another embodiment of a microscope according to the present invention. The microscope comprises a first semiconductor laser 3 and a further semiconductor laser 5 that is embodied as UV laser 59. Illuminating light 61 emitted by first semiconductor laser 3 arrives at a first illumination pinhole 63 and, after traversing illumination pinhole 63, is directed by dichroic beam splitter 65 to beam deflection device 17, which contains a gimbal-mounted scanning mirror 19. Second illuminating light 67 emitted by further semiconductor laser 5 travels to a second illumination pinhole 69 and then to a second dichroic beam splitter 71 that guides second illuminating light 67 once again to beam deflection device 17. Beam deflection device 17 directs first and second illuminating light 61, 67 through the scanning optical system (not shown), the tube optical system (not shown), and the objective (not shown), and over or through sample 27. Detected light 29 proceeding from the sample travels via beam deflection device 17 through dichroic beam splitters 65, 71 to detection pinhole 73, traverses the latter and the downstream filter wheel 75, and then arrives at a further dichroic beam splitter 77 that distributes detected light 29 onto a first detection channel 79 and a second detection channel 81. A first detection filter 83, which prevents extraneous light (e.g. excitation light still present in the detected light) from arriving at first detector 85, is arranged in first detection channel 79. A second detection filter 84 that keeps extraneous light away from second detector 87 is likewise provided in second detection channel 81. A deflection element 89 can be introduced into the beam path between detection pinhole 73 and further dichroic beam splitter 77 in order to direct detected light 29 onto a multi-band detector 91 in order to generate an image of the sample. First detector 85 and second detector 87 generate electrical signals, proportional to the number of arriving detected photons, that are transferred to a processing unit 47. Processing unit 47 is embodied as a PC 49, and preferably contains a Becker+Hickl SPC 730-830 plug-in card 50. The result of the FLIM investigation is displayed graphically on a monitor 51.

The invention has been described with reference to particular embodiments. It is self-evident, however, that changes and modifications can be made without thereby leaving the range of protection of the claims below.

What is claimed is:

1. A scanning confocal microscope for investigating the lifetime of excited states in a sample comprising:
    at least one light source that comprises a semiconductor laser which emits pulsed excitation light and configured to excite a first fluorescent dye;
    at least one further semiconductor laser configured to excite a second fluorescent dye;
    at least one detector that receives detected light proceeding from the sample; and
    an adjusting apparatus for adjusting the pulse repetition rate to the specific lifetime properties of the sample
    wherein the semiconductor laser and the at least one further semiconductor laser are synchronized with one another.

2. The microscope as defined in claim 1, wherein the excitation in the sample encompasses a one-photon transition.

3. The microscope as defined in claim 1, wherein the excitation in the sample encompasses a multi-photon transition, in particular a two-photon transition.

4. The microscope as defined in claim 1, wherein the at least one further semiconductor laser emits further pulsed excitation light.

5. The microscope as defined in claim 1, further comprising control apparatus that controls the current operating the semiconductor laser.

6. The microscope as defined in claim 5, wherein the control apparatus generates electrical detection start signals synchronously with the pulses of the excitation light and/or of the further excitation light.

7. The microscope as defined in claim 1, wherein the semiconductor laser and the detector are synchronized with one another.

8. The microscope as defined in claim 1, wherein the repetition rate of the semiconductor laser is continuously adjustable.

9. The microscope as defined in claim 1, wherein the repetition rate of the semiconductor laser is adjustable in steps.

10. The microscope as defined in claim 9, wherein the repetition rate of the semiconductor laser is adjustable in steps to 40 MHz, 20 MHz, 10 MHz, and 5 MHz.

11. The microscope as defined in claim 1, wherein the further semiconductor laser encompasses a titanium sapphire laser.

12. The microscope as defined in claim 1, wherein the detector has one detection channel.

13. The microscope as defined in claim 1, wherein the detector has multiple detection channels.

14. The microscope as defined in claim 1, wherein the detector contains a nondescan detector.

15. The microscope as defined in claim 1, wherein the detector contains a descan detector.

16. The microscope as defined in claim 1 wherein the investigating is included in a fluorescence resonance energy transfer investigation.

17. The microscope as defined in claim 1, further comprising an illumination pinhole that passes the pulsed excitation light therethrough.

18. The microscope as defined in claim 1, further comprising a beam deflection device for guiding the pulsed excitation light over or through the sample.

\* \* \* \* \*